United States Patent [19]

Nöltner et al.

[11] 4,244,776
[45] Jan. 13, 1981

[54] FLUIDIZED BED TREATMENT OF GRANULAR POTASSIUM SORBATE

[75] Inventors: Gerhard Nöltner, Frankfurt am Main; Horst Oehme, Bad Soden am Taunus; Rudolf Lademann, Kelkheim; Heinz Wendt, Sulzbach, all of Fed. Rep. of Germany

[73] Assignee: Hoechst Aktiengesellschaft, Frankfurt am Main, Fed. Rep. of Germany

[21] Appl. No.: 18,731

[22] Filed: Mar. 8, 1979

[30] Foreign Application Priority Data

Mar. 11, 1978 [DE] Fed. Rep. of Germany ..... 28107020

[51] Int. Cl.$^3$ ............................................. C07C 57/10

[52] U.S. Cl. .................................. 159/48 R; 159/4 E; 159/DIG. 3; 159/DIG. 10; 159/16 R; 562/601

[58] Field of Search ..... 562/601; 159/16 R, DIG. 10, 159/48 R, DIG. 3, 4 E

[56] References Cited

U.S. PATENT DOCUMENTS

| | | |
|---|---|---|
| 3,112,220 | 11/1963 | Heiser, Jr. et al. ................ 159/4 E |
| 3,173,948 | 3/1965 | Probst et al. ....................... 562/601 |
| 3,533,829 | 12/1966 | Quanquin ........................ 159/16 R |

Primary Examiner—Norman Yudkoff
Attorney, Agent, or Firm—Curtis, Morris & Safford

[57] ABSTRACT

Granular potassium sorbate is continuously manufactured by spraying an aqueous potassium sorbate solution into or onto a bed of potassium sorbate particles fluidized by heated air.

9 Claims, 1 Drawing Figure

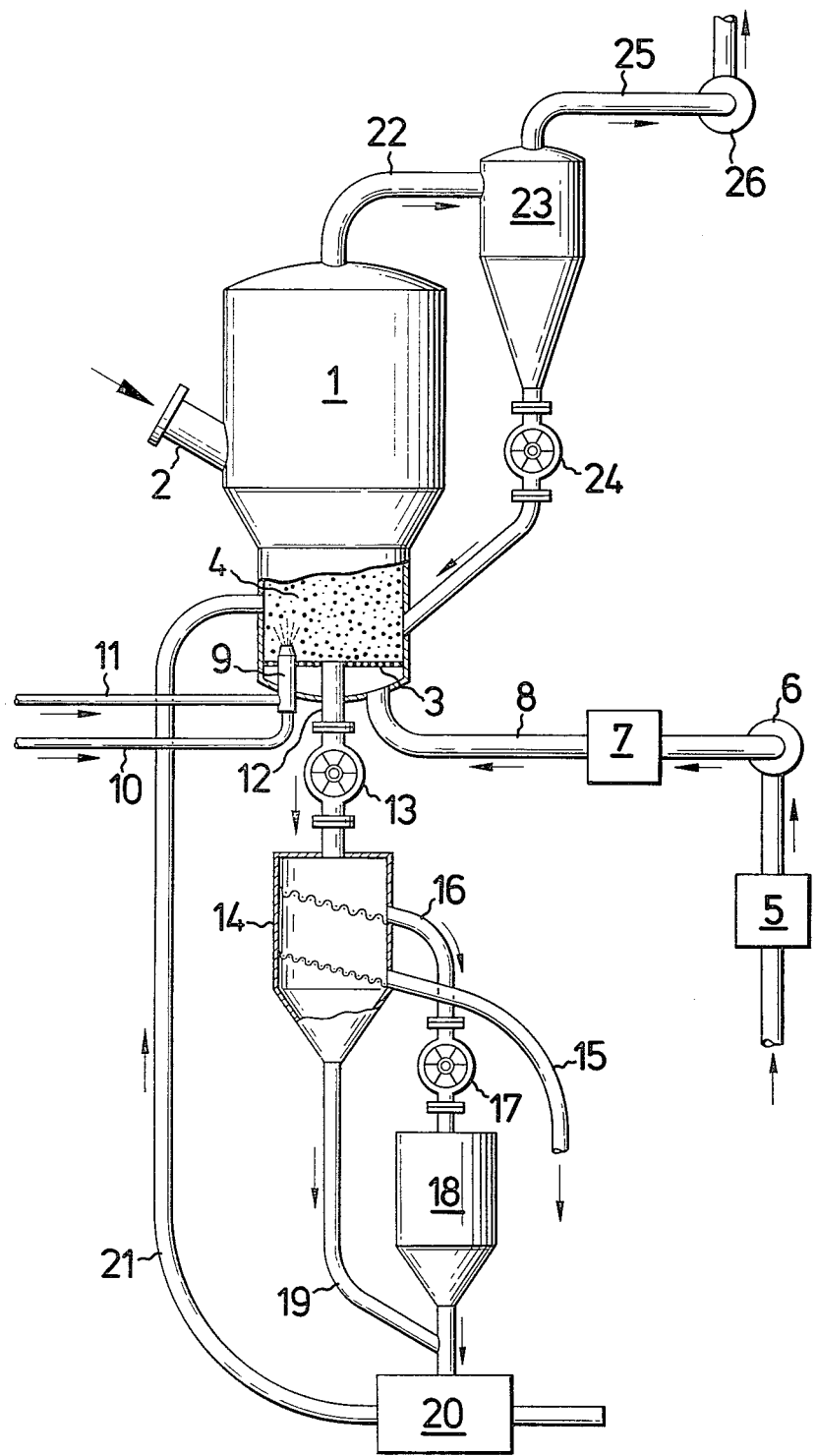

FLUIDIZED BED TREATMENT OF GRANULAR POTASSIUM SORBATE

For the preservation of food, sorbic acid is preferably used in the form of the easily hydrosoluble potassium salt. Recently, this potassium sorbate is more and more applied in the form of granules.

It is known that potassium sorbate exhibits the properties of sensitivity to moisture, agglomeration, discoloration in air due to decomposition, and alteration of smell. Because of their reduced surface, granules have a better storage stability than the pulverulent product which is obtained from a concentrated aqueous solution by means of spray drying or crystallization.

For the preparation of granular potassium sorbate, various processes have been previously described. They start from a moist, moldable paste which is obtained either from dry potassium sorbate by adding water (German Offenlegungsschrift No. 26 17 745) or from a concentrated salt solution by partial evaporation (German Auslegeschrift No. 24 50 184). This paste is extruded to strands in commercial extruders, cut and dried in suitable driers to a residual moisture of about 0.1%.

Because of the abovementioned risk of decomposition, the known granulating processes attempt to reduce the processing time as much as possible (German Auslegeschrift No. 24 50 184), or to use other solvents such as lower alcohols, ketones, fatty acid esters or mixtures thereof with water instead of water alone for the manufacture of the paste to be granulated (German Offenlegungsschrift No. 26 17 745).

Since the sensitivity to water of the potassium sorbate increases with rising temperatures, the known granulating processes require expensive drying equipment which must be operated with extreme care because of the low mechanical stability of the moist extruded granules. Moreover, the residual moisture of less than 0.2% required to obtain a stable, storable product can be attained only under reduced pressure, otherwise the quality would be adversely affected, for example by discoloration due to excessive high temperatures and an excessively long residence time in the drying equipment.

For the extrusion of the commercial, cylindrical granules having a diameter of about 1 mm, a die is required in which the holes of are easily plugged due to the randomly distributed residual moisture in the paste to be extruded. According to German Offenlegungsschrift No. 26 17 745, a uniform moisture distribution is obtained; however, this requires a considerably prolonged residence time which may cause discoloration by decomposition.

When the material is partially dried according to German Auslegeschrift No. 24 50 184 to obtain the residual water content required for machine extrusion, the flocklike agglomerates exhibit a considerably lower moisture content on the surface than in their core.

These difficulties would be overcome by dry granulation; however, the suitable tablet compressing or compacting equipment require very high pressures, since binders cannot be employed for food additives. Moreover, the highly compressed granules so obtained have such a low solubility rate in water that their practical application in the food industry (nearly exclusively in the form of an aqueous solution) is almost impossible.

It is therefore the object of the present invention to provide a granulating process for potassium sorbate which ensures that the quality of the granules is not deteriorated by decomposition or discoloration.

In accordance with this invention, there is provided a process for the continuous manufacture of granular sorbate, which comprises spraying an aqueous potassium sorbate solution into or onto a bed of potassium sorbate particles fluidized by heated air; the amount of potassium sorbate solution per unit of time being adjusted in such a manner that the temperature of the fluidized bed is in the range of from 40° to 80° C. and the relative humidity of the air leaving the fluidized bed does not exceed 20 weight %, relative to 60° C.

The concentration of the potassium sorbate solution is preferably at least 30%, especially at least 50%. The upper limit is set by the solubility of the potassium sorbate in water, which is about 58 weight % at 20° C.

German Offenlegungsschrift No. 2 231 445 proposes already a process for the manufacture of granules by spraying a solution or suspension onto a fluidized bed. However, in this process considerable amounts of granules which already have the desired grain size are recycled to the fluidized bed. In the case of potassium sorbate, such recycling would rapidly produce a considerable amount of excessively large grains which would have to be comminuted before recycling to the fluidized bed. Since such comminution would put thermal strain upon the granular potassium sorbate, the amount of granules to be crushed and recycled must be kept as low as possible. This is achieved by the process of the invention.

The process of the invention yields flowable granular potassium sorbate and consists of solid, generally spherically-shaped particles. Therefore, it can be handled with no or only an insignificant amount of dust formation and can still be dissolved very easily and rapidly in water.

By the process of the invention moist potassium sorbate is subjected for only a short time to temperatures of from 40° to 80° C., because the potassium sorbate solution sprayed into or onto the fluidized bed deposits on the potassium sorbate particles of this bed and the water evaporates immediately. The moisture content of the granules which are formed always remains below 0.2 weight %.

In the process of the invention, the temperature of the air required for forming the fluidized bed and for driving off the evaporated water is adjusted in such a manner that the temperature of the fluidized bed is from 40° to 80° C., preferably 55° to 75° C., and especially 55° to 70° C. Generally, the fluidizing air has a temperature of from 100° to 160° C., preferably 120° to 140° C., before it is contacted with the bed.

By evaporation of the water sprayed into the fluidized bed in the form of a potassium sorbate solution, the temperature of the fluidizing air drops as soon as it is contacted with the bed, and simultaneously, it is enriched with the evaporated water. The amount of potassium sorbate solution sprayed in per unit of time is chosen in such a manner that the temperature of the fluidized bed and the relative moisture of the air leaving the bed attain the values in accordance with this invention. In the case of high atmospheric humidity, it is advantageous to dry the fluidizing air before it is sprayed into the bed. The potassium sorbate solution is sprayed via single-component or binary nozzles.

In the process of the invention, there is no need for a partial or complete evaporation of the potassium sorbate solution as required by the known extrusion granulation, method wherein prior to the evaporation (after which the sorbate sometimes has to be moistened again) an extrudable material has to be prepared. An expensive after-drying of the finished granular material is also no longer necessary. Thus, the novel process provides a rapid, though still gentle, manufacture of dry granules in a single step.

The present invention results in a gentle method of granular potassium sorbate manufacture wherein any discoloration by decomposition is reduced to an insignificant amount, which can be determined by measuring the permeability to light of an aqueous solution.

The invention will be better understood by reference to the accompanying drawing which shows an example of an apparatus which is suitable for the process of the invention. The use of similar equipment is already described in German Offenlegungsschrift Nos. 2 231 445 and 2 263 968.

Dry potassium sorbate in pulverulent or, preferably, granular form is fed via tube (2) to the perforated bottom (3) of the cyclindrical granulating and drying chamber (1) with a diameter of 1.6 m, where it is swirled to create a fluidized bed (4). The fluidizing air required is aspirated from the atmosphere via the air drier (5) by means of the fan (6), heated in the air heater (7) and introduced into the chamber (1) via duct (8) below the horizontally positioned perforated bottom (3). Simultaneously, aqueous potassium sorbate solution is sprayed into the fluidized bed (4) through several binary nozzles which project into the fluidized bed passing through the perforated bottom plate from below (one of them (9) only being shown in the drawing). The sorbate solution is fed to the nozzles via duct (10) and fluidizing air is supplied via duct (11). The fluidizing air enters the chamber (1) at a temperature of from 100° to 160° C. Evaporation of the water sprayed into the fluidized bed (4) in the form of the potassium sorbate solution decreases the temperature of the fluidizing air as soon as it is contacted with the bed. By correspondingly adjusting the amount of potassium sorbate solution sprayed in per unit of time, the temperature of the fluidizing air above the perforated bottom (3) and thus the temperature of the fluidized bed is adjusted at 40° to 80° C., and the relative moisture of the air leaving the bed to a maximum 20% (relative to 60° C.). The potassium sorbate granules prepared in the chamber (1) are continuously discharged via the tube (12) arranged in the center of the perforated bottom plate (3) and the rotary valve (13), and separated in the screening device (14). The granules having the intended size are removed via duct (15). In order to maintain a stationary fluidized bed, the amount of granules discharged from chamber (1) corresponds to the amount of potassium sorbate sprayed in. The fraction which is too coarse is forwarded via duct (16) and rotary valve (17) to the mill (18), where it is comminuted. This comminuted material, as well as the too finely grained fraction (via duct (19)) is forwarded to the pneumatic conveyer (20) and recycled to the chamber (1) via duct (21). The fluidizing air is forwarded from the chamber (1) via duct (22) to a cyclone (23), where entrained potassium sorbate is separated, out and then recycled to the chamber (1) via rotary valve (24). The fluidizing air purified in the cyclone (23) is driven off into the open atmosphere via duct (25) and the fan (26).

The granular potassium sorbate manufactured according to the process of the invention is distinguished by its properties of being easily handled. Because of its generally spherically-shaped structure (sphere diameter of about 0.5 to 1.5 mm) it has good flowability. It is very resistant to abrasion and thus practically dustless. It is therefore superior to the granules manufactured by extrusion which, due to their cylindrical form, are prone to abrasion to a much larger extent. Moreover, the manufacture of the granules itself proceeds without significant abrasion, in contrast to the extrusion manufacture of granules.

The following examples illustrate the invention.

EXAMPLE 1

1.200 kg of granular potassium sorbate are introduced as fluidized bed into the granulating and drying chamber (1). Below the perforated bottom (3), 10.000 nm$^3$/h of air having a temperature of 135° C. and a water content of 7 g per kg of dry air (corresponding to a relative moisture of 48%, relative to 20° C.) is introduced. Simultaneously, a 50% potassium sorbate solution (475 l/h = 500 kg/h) is sprayed by means of spraying air compressed to about 1.3 bars (1000 nm$^3$/h) into the fluidized bed (4) via duct (10) and nozzles (9) arranged in a circle and projecting through the perforated bottom (3), so that a bed temperature of 65° C. is obtained. The water amount of 250 kg/h contained in the potassium sorbate solution, which evaporates, gives a water content in the air leaving the fluidized bed of about 25.4 g per kg of dry air, corresponding to a relative moisture of less than 20%, relative to 60° C. The granules formed have a bulk density of 740 g/liter and a residual moisture of 0.1% and are removed continuously via duct (12) and separated in the screening device (14). On the average, the following distribution of grain sizes is obtained:

10 weight %: more than 1.6 mm
60 weight %: 1.0 to 1.6 mm
30 weight %: 0.5 to 1.0 mm An insignificant amount (less than 1 weight %) of fine grains smaller than 0.5 mm, as well as the amount of coarse grains (10 weight %) having a size of more than 1.6 mm after having passed through the comminution device (18), are recycled to the lower part of the fluidized bed near the nozzles. The amount of dust separated from the leaving air in a cyclone lone is recycled before this air leaves the apparatus via a fan.

Discoloration Test

In a photometer, at a wave length of 400 nm, the permeability to light of three samples is measured; pure water (100% permeability to light) serving as a standard of comparison:

1. 50% potassium sorbate solution (like the solution sprayed into the fluidized bed): 96.5% permeability to light
2. 12% aqueous solution of granule fraction of 0.5 to 1.5 mm: 95.0% permeability to light
3. 12% aqueous solution of granule fraction of 0.5 to 1.5 mm, which had been stored for 6 months at 25° C.: 94% permeability to light.

Solubility Test 25 g of the granule fraction of 0.5 to 1.5 mm are mixed in a beaker with 100 ml of deionized water, and the time it takes until the granules are completely dissolved is measured:

1. without agitation: 100 seconds
2. with agitation: 11 seconds

COMPARATIVE EXAMPLE 1

Same procedure as in Example 1; however, for the formation of the fluidized bed, air containing 11 g of water per kg of dry air, corresponding to a relative humidity of 75% relative to 20° C. is used. At identical bed temperature of 65° C. and identical throughput of 50% potassium sorbate solution, the relative humidity of the air leaving the fluidized bed is 23% relative to 60° C., corresponding to a water content of 29 g per kg of dry air. As compared to Example 1, considerably coarser granules are obtained having a mean bulk density of 710 g/liter and the following distribution of grain sizes:

90 weight %: more than 1.6 mm
6 weight %: 1.0 to 1.6 mm
4 weight %: 0.5 to 1.0 mm The residual moisture of the grain fraction of more than 1.6 mm is 0.25% on the average. The spherically-shaped particles (part of which have a size of up to 5 mm) of more than 1.6 mm initially show a permeability to light of 95% in 12% aqueous solution in the discoloration test (see Example 1). After 6 months of storage however, the granules have discolored to yellow-brown, and the permeability to light is only 76%.

Solubility test (as in Example 1)

1. without agitation: 700 seconds
2. with agitation: 24 seconds

That means that the granules have a considerably poorer solubility than those prepared according to Example 1.

COMPARATIVE EXAMPLE 2

Potassium sorbate powder having 0.1% of residual moisture, obtained by spray drying from 50% aqueous potassium sorbate solution, is mixed with 8% (relative to potassium sorbate) of water in a screw mixer trough to form a paste. In an extruder, this paste is extruded to strands by means of a die having holes of a diameter of 1.3 mm, and these strands are cut to give cylindrical pieces of a length of about 5 mm. Subsequently, they are predried with warm air having a temperature of 53° C. After 5 minutes, a residual moisture of 3% is attained which ensures a mechanical stability of the granules sufficient for continuous drying in a commercial vacuum drier. After 90 minutes of drying at 65° C. in vacuo, the required residual moisture in the granules of 0.1% is attained. The average bulk density of the granules is 540 g/liter.

Discoloration test 1. 50% potassium sorbate solution (like the solution used in spray drying procedure): 96.5% permeability to light
2. 12% aqueous solution of the potassium sorbate powder obtained by spray drying: 95.0% permeability to light
3. 12% aqueous solution of the granules: 96.0% permeability to light
4. 12% aqueous solution of the granules stored for 6 months at 25° C.: 86.0% permeability to light Solubility test of the granules (as in Example 1)

1. without agitation: 50 seconds
2. with agitation: 10 seconds

What is claimed is:

1. A process for the continuous manufacture of potassium sorbate, which comprises contacting an aqueous potassium sorbate solution with a bed of potassium sorbate particles fluidized by heated air wherein the amount of potassium sorbate solution contacted with the fluidized bed is adjusted in such a manner that the temperature of the fluidized bed is from 40° to 80° C. and the relative humidity of the air leaving the fluidized bed does not exceed 20 weight %, relative to 60° C.

2. The process as claimed in claim 1, wherein the temperature of the fluidized bed is from 55° to 75° C.

3. The process as claimed in one of claims 1 or 2, which comprises heating the air used for fluidizing the bed to a temperature of from 100° to 160° C. before contacting it with the bed.

4. The process as claimed in one of claims 1 or 2, which comprises heating the air used for fluidizing the bed to a temperature of from 120° to 140° C. before contacting it with the bed.

5. The process as claimed in claim 1, wherein the temperature of the fluidized bed is from 55° to 70° C.

6. The process as claimed in claim 3 which comprises heating the air used for fluidizing the bed to a temperature of from 100° to 160° C. before contacting it with the bed.

7. The process as claimed in claim 3 which comprises heating the air used for fluidizing the bed to a temperature of from 120° to 140° C. before contacting it with the bed.

8. The process as claimed in claim 1 wherein the concentration of the aqueous potassium sorbate solution is at least 30% by weight.

9. The process as claimed in claim 1 wherein the concentration of the aqueous potassium sorbate solution is at least 50% by weight.

* * * * *